United States Patent
Oki et al.

(10) Patent No.: US 11,278,183 B2
(45) Date of Patent: Mar. 22, 2022

(54) LIGHT SOURCE DEVICE AND IMAGING SYSTEM

(71) Applicant: SONY CORPORATION, Tokyo (JP)

(72) Inventors: Tomoyuki Oki, Kanagawa (JP); Akio Furukawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 983 days.

(21) Appl. No.: 15/775,867

(22) PCT Filed: Oct. 28, 2016

(86) PCT No.: PCT/JP2016/082167
§ 371 (c)(1),
(2) Date: May 14, 2018

(87) PCT Pub. No.: WO2017/115552
PCT Pub. Date: Jul. 6, 2017

(65) Prior Publication Data
US 2018/0330659 A1 Nov. 15, 2018

(30) Foreign Application Priority Data
Dec. 28, 2015 (JP) .............................. JP2015-256136

(51) Int. Cl.
*A61B 1/04* (2006.01)
*A61B 1/06* (2006.01)
(Continued)

(52) U.S. Cl.
CPC ...... *A61B 1/00006* (2013.01); *A61B 1/00055* (2013.01); *A61B 1/00057* (2013.01);
(Continued)

(58) Field of Classification Search
CPC ......... A61B 1/0684; G09G 3/22; G02B 23/26
See application file for complete search history.

(56) References Cited

U.S. PATENT DOCUMENTS 6,320,331 B1 * 11/2001 Iida ........................ H05B 47/20
315/293
2009/0109409 A1 4/2009 Haraguchi et al.
(Continued)

FOREIGN PATENT DOCUMENTS

| JP | H03-232287 A | 10/1991 |
| JP | 1997-002887 | * 10/1996 |

(Continued)

OTHER PUBLICATIONS

International Search Report dated Dec. 13, 2016 in PCT/JP2016/082167.
(Continued)

*Primary Examiner* — Alexandra L Newton
*Assistant Examiner* — Rynae E Boler
(74) *Attorney, Agent, or Firm* — Xsensus LLP

(57) ABSTRACT

[Object] To provide a light source device and imaging system capable of issuing a warning to a user in accordance with an actual deterioration state of a light source.
[Solution] The light source device includes: at least one light source; a light monitor unit that detects emitted light emitted from the light source; a light source drive unit that controls a drive current or an applied voltage of the light source such that a detection value detected by the light monitor unit indicates a predetermined target value; and a warning unit
(Continued)

that performs a primary warning when the drive current or the applied voltage of the light source reaches a predetermined reference value, and performs a predetermined process on a basis of a deterioration level of the light source after the primary warning is performed.

18 Claims, 14 Drawing Sheets

(51) Int. Cl.
*G09G 3/22* (2006.01)
*A61B 1/00* (2006.01)
*G02B 23/24* (2006.01)
*H05B 45/50* (2022.01)
*H01S 5/22* (2006.01)

(52) U.S. Cl.
CPC .............. *A61B 1/04* (2013.01); *A61B 1/0638* (2013.01); *A61B 1/0661* (2013.01); *A61B 1/0684* (2013.01); *G02B 23/24* (2013.01); *G09G 3/22* (2013.01); *H01S 5/2228* (2013.01); *H05B 45/50* (2020.01); *G09G 2310/0264* (2013.01)

(56) References Cited

U.S. PATENT DOCUMENTS

| | | |
|---|---|---|
| 2013/0271732 A1 | 10/2013 | Kuriaki et al. |
| 2015/0099932 A1 | 4/2015 | Morimoto et al. |
| 2017/0099421 A1* | 4/2017 | Nakajima ................ H04N 3/02 |

FOREIGN PATENT DOCUMENTS

| | | |
|---|---|---|
| JP | 2000-66117 A | 3/2000 |
| JP | 2000-180732 A | 6/2000 |
| JP | 2008-301873 A | 12/2008 |
| JP | 2009-122651 A | 6/2009 |
| JP | 2009-200242 A | 9/2009 |
| JP | 2013-222064 A | 10/2013 |
| JP | 2015-70946 A | 4/2015 |

OTHER PUBLICATIONS

Office Action dated Oct. 13, 2020, in corresponding Japanese patent Application No. 2017-558872, 8 pages.

* cited by examiner

NORMAL STATE

PRIMARY WARNING
(EXAMPLE: CASE WHERE R LIGHT SOURCE HAS DETERIORATED)

SECONDARY WARNING
(EXAMPLE: CASE WHERE ONLY UP TO LEVEL 5 CAN BE USED)

NORMAL STATE

PRIMARY WARNING
(EXAMPLE: CASE WHERE R LIGHT SOURCE HAS DETERIORATED)

SECONDARY WARNING
(EXAMPLE: CASE WHERE ONLY UP TO LEVEL 5 CAN BE USED)

LIGHT SOURCE DEVICE AND IMAGING SYSTEM

TECHNICAL FIELD

The present disclosure relates to a light source device and an imaging system.

BACKGROUND ART

In the past, endoscopes have come to be widely used as instruments to see the inside of objects. In particular, in a medical field, endoscopes have spread rapidly with the development of surgical procedure technology and are currently indispensable instruments in a variety of medical fields. With endoscopic devices thus far, a lamp light source such as a xenon lamp or a halogen lamp is used as an illuminating light source, whether it be for flexible endoscopes or rigid endoscopes. One characteristic of such a lamp light source is that the light amount of emitted light cannot be electrically adjusted. Therefore, in order to adjust the light amount with the lamp light source, the light amount is mechanically stopped down by an aperture mechanism while shining the lamp light source at a constant output, so as to obtain illumination light according to the light amount level set by a user.

The load with respect to the lamp light source is always constant regardless of the light amount level. Therefore, as a typical countermeasure against deterioration of the lamp light source, the cumulative lighting time is counted, and replacement is recommended when the cumulative lighting time reaches a preset life (see Patent Literature 1, for example).

CITATION LIST

Patent Literature

Patent Literature 1: JP 2000-66117A

DISCLOSURE OF INVENTION

Technical Problem

In actuality, however, it is difficult to accurately grasp the replacement timing because the life of the lamp light source varies depending on the usage environment. Therefore, in order to prevent the light amount from decreasing during use, with many lamp light sources, it is recommended that the lamp light source be changed regularly assuming a life with time to spare. In particular, in the case of an endoscopic device used in a medical field, it is necessary to prevent the light amount from decreasing during surgery, so a life with time to spare is predicted.

Also, recently, there are light source devices that use a light emitting element capable of electrically adjusting the light amount, which are typified by a light emitting diode (LED) and a laser diode (LD) and the like, instead of a lamp light source. A light emitting element has a longer life than a lamp light source and is often maintenance free. However, deterioration also occurs to no small extent in light emitting elements depending on the usage environment, so it is desirable to give some sort of warning to the user. Although the cumulative lighting time and the replacement timing of a light emitting element can also be managed, similar to a lamp light source, the life no less varies depending on the usage environment, which makes it difficult to accurately grasp the replacement timing. In particular, with a light emitting element, the degree of deterioration can change greatly depending on the light amount during use and the usage environment, so it is difficult to uniformly predict the replacement timing.

Therefore, the present disclosure proposes a new and improved light source device and imaging system capable of issuing a warning to a user in accordance with an actual deterioration state of a light source.

Solution to Problem

According to the present disclosure, there is provided a light source device including: at least one light source; a light monitor unit that detects emitted light emitted from the light source; a light source drive unit that controls a drive current or an applied voltage of the light source such that a detection value detected by the light monitor unit indicates a predetermined target value; and a warning unit that performs a primary warning when the drive current or the applied voltage of the light source reaches a predetermined reference value, and performs a predetermined process on a basis of a deterioration level of the light source after the primary warning is performed.

In addition, according to the present disclosure, there is provided an imaging system including: at least one light source; a light monitor unit that detects emitted light emitted from the light source; a light source drive unit that controls a drive current or an applied voltage of the light source such that a detection value detected by the light monitor unit indicates a predetermined target value; a warning unit that performs a primary warning when the drive current or the applied voltage of the light source reaches a predetermined reference value, and performs a predetermined process on a basis of a deterioration level of the light source after the primary warning is performed; and an imaging unit that images an irradiation object that is illuminated.

Advantageous Effects of Invention

As described above, according to the present disclosure, it is possible to issue a warning to a user in accordance with an actual deterioration state of a light source. Note that the effects described above are not necessarily limitative. With or in the place of the above effects, there may be achieved any one of the effects described in this specification or other effects that may be grasped from this specification.

MODE(S) FOR CARRYING OUT THE INVENTION

Figure 1:
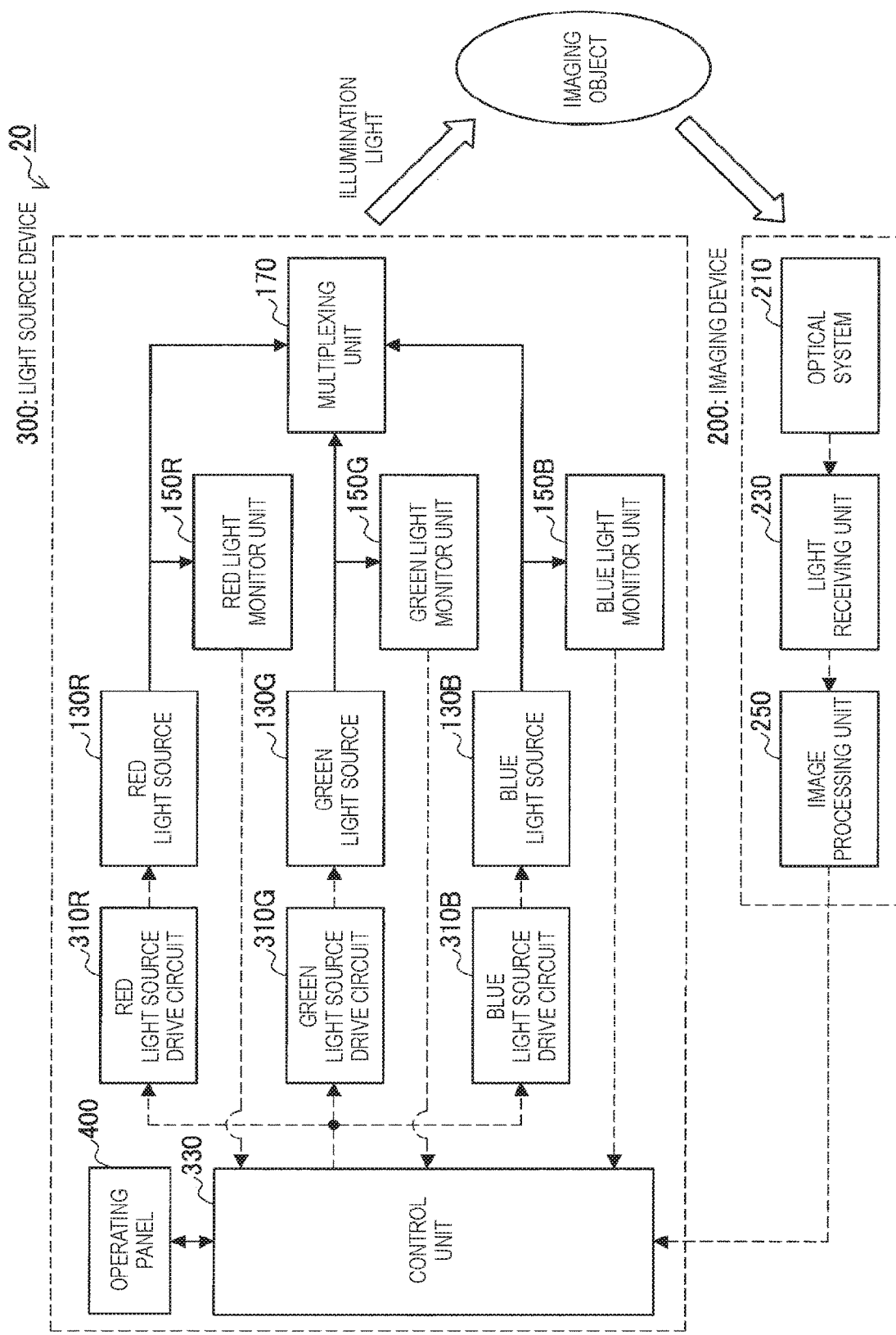
FIG. 1 is a block diagram illustrating an imaging system according to an embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be given in the following order.

1. Overall configuration of imaging system
    1-1. Configuration example of light source device
    1-2. Configuration example of imaging device
2. Control process of light source device
    2-1. Outline of control process
    2-2. Target value learning process
    2-3. Light source driving process
    2-4. Deterioration determination process
3. Examples of warning process
    3-1. Example in which warning display is performed for each light source
    3-2. Example in which warning display is performed for light source device as a whole
4. Conclusion
5. Modified examples
    5-1. First modified example (example in which color sensor is used)
    5-2. Second modified example (example in which one light source is provided)

Hereinafter, in the present specification, the term "emitted light" will refer to light emitted from a light source, and the term "illumination light" will refer to light output from a light source device.

1. Overall Configuration of Imaging System

First, the general configuration of an imaging system 20 provided with a light source device 300 according to an embodiment of the present disclosure will be described with reference to FIG. 1. FIG. 1 is a block diagram illustrating the overall configuration of the imaging system 20 according to the present embodiment. The imaging system 20 includes the light source device 300 and an imaging device 200, and is configured as a medical endoscopic device, for example. The imaging device 200 corresponds to an imaging unit in the technology of the present disclosure. An endoscopic device is one example of the imaging system 20, but the imaging system 20 may be another system such as an electron microscope.

1-1. Configuration Example of Light Source Device

The light source device 300 includes a red light source 130R, a green light source 130G, a blue light source 130B, a red light source drive circuit 310R, a green light source drive circuit 310G, a blue light source drive circuit 310B, a multiplexing unit 170, a control unit 330, and an operating panel 400. The light source device 300 also includes a red light monitor unit 150R, a green light monitor unit 150G, and a blue light monitor unit 150B.

Hereinafter, the red light source 130R, the green light source 130G, and the blue light source 130B are also collectively be referred to as light sources 130. Also, the red light source drive circuit 310R, the green light source drive circuit 310G, and the blue light source drive circuit 310B are also collectively be referred to as light source drive circuits 310. Furthermore, the red light monitor unit 150R, the green light monitor unit 150G, and the blue light monitor unit 150B are also collectively be referred to as light monitor units 150.

1-1-1. RGB Light Source

The red light source 130R is formed by a semiconductor laser such as a GaInP quantum-well laser diode, for example, and emits light in a wavelength range of 630 to 645 nm, for example. The blue light source 130B is formed by a semiconductor laser such as a GaInN quantum-well laser diode, for example, and emits light in a wavelength range of 435 to 465 nm, for example. The green light source 130G is formed by a solid-state laser excited by a semiconductor laser, for example, and emits light in a wavelength range of 510 to 540 nm, for example. With the light source device 300 according to the present embodiment, the RGB light source is formed by a three-color light source controlled by a semiconductor laser, and, unlike a lamp light source such as a xenon lamp or a halogen lamp, the light amount of the emitted light is able to be electrically adjusted.

Note that the semiconductor laser or the solid-state laser described above is one example of the light source 130. Another type of light source may be used as long as it is a light source in which the light amount can be electrically adjusted. However, with a laser light source, diffusion of the emitted light is small, so the light amount is easily detected by a light monitor unit in a case where a laser light source is used. Also, the light source 130 is not limited to a three-color light source, and may be a four-color light source or the like, and the number of light sources is not limited.

1-1-2. Drive Circuit

The red light source drive circuit 310R, the green light source drive circuit 310G, and the blue light source drive circuit 310B drive the red light source 130R, the green light source 130G, and the blue light source 130B, respectively, on the basis of a drive command generated by the control unit 330. For example, the light source drive circuit 310 has a circuit configuration capable of adjusting a drive current $I_r$, $I_g$, and $I_b$ to each of the light sources 130. Note that the light source device 300 according to the present embodiment is configured as a continuous irradiation type light source device in which each light source continuously emits light.

1-1-3. Light Monitor Unit

The red light monitor unit 150R, the green light monitor unit 150G, and the blue light monitor unit 150B detect the light amount of emitted light from the red light source 130R, the green light source 130G, and the blue light source 130B, respectively. For example, the light monitor units 150 are formed by a photodiode and receive some of the emitted light emitted from each of the light sources 130, convert the light amount of the received light to a voltage signal, and transmit the voltage signal to the control unit 330.

1-1-4. Multiplexing Unit

The multiplexing unit 170 multiplexes red light, green light, and blue light emitted from the red light source 130R, the green light source 130G, and the blue light source 130B, respectively. In the light source device 300 according to the present embodiment, the color temperature of the illumination light after multiplexing is adjusted by adjusting each light amount of the red light, the green light, and the blue light.

Figure 2:
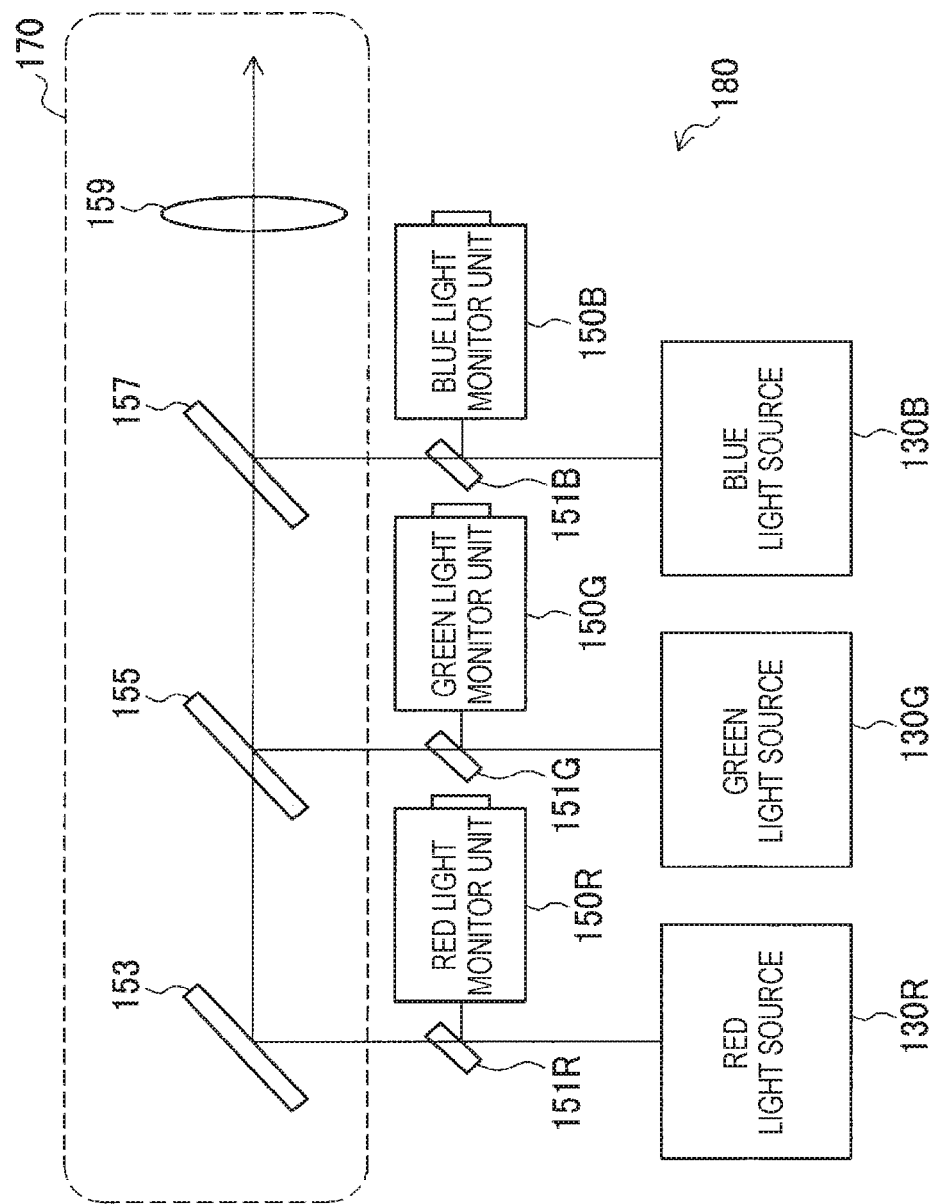
FIG. 2 is a schematic diagram illustrating an RGB multiplexing module having a light monitor unit.

FIG. 2 is a schematic diagram illustrating a configuration example of a multiplexing module 180 equipped with a light monitor, and which includes the multiplexing unit 170. In this multiplexing module 180, the multiplexing unit 170 includes a mirror 153 and dichroic mirrors 155 and 157. The dichroic mirrors 155 and 157 each reflect light of a specific wavelength, while allowing light of other wavelengths to pass through. In the example in FIG. 2, red light emitted from the red light source 130R is reflected by the mirror 153, and the path thereof is changed toward a lens 159. The mirror 153 may also be a dichroic mirror.

Green light emitted from the green light source 130G is reflected by the dichroic mirror 155, and the path thereof is changed toward the lens 159. At this time, the red light sent from the mirror 153 passes directly through the dichroic mirror 155. Also, blue light emitted from the blue light source 130B is reflected by the dichroic mirror 157, and the path thereof is changed toward the lens 159. At this time, the red light and green light sent from the dichroic mirror 155 pass directly through the dichroic mirror 157.

In this way, light of each color of R, G, and B is directed on the same optical axis and superimposed. In the example of the multiplexing module 180, the green light having the second longest wavelength is multiplexed with the red light having the longest wavelength, and the blue light having the shortest wavelength is further multiplexed thereon. The multiplexed light is further collected by the lens 159 and emitted as illumination light. In the case of the endoscopic system according to the present embodiment, the emitted illumination light is directed to a distal end of the endoscopic probe and radiated therefrom to illuminate a target portion.

In the multiplexing module 180, some of the red light emitted from the red light source 130R is input into the red light monitor unit 150R using a light sampler 151R before being multiplexed. As a result, the light amount of the red light can be detected. Similarly, some of the green light and the blue light emitted from the green light source 130G and the blue light source 130B are input into the green light monitor unit 150G or the blue light monitor unit 150B using light samplers 151G and 151B, so the light amounts can be detected.

1-1-5. Control Unit

Figure 3:
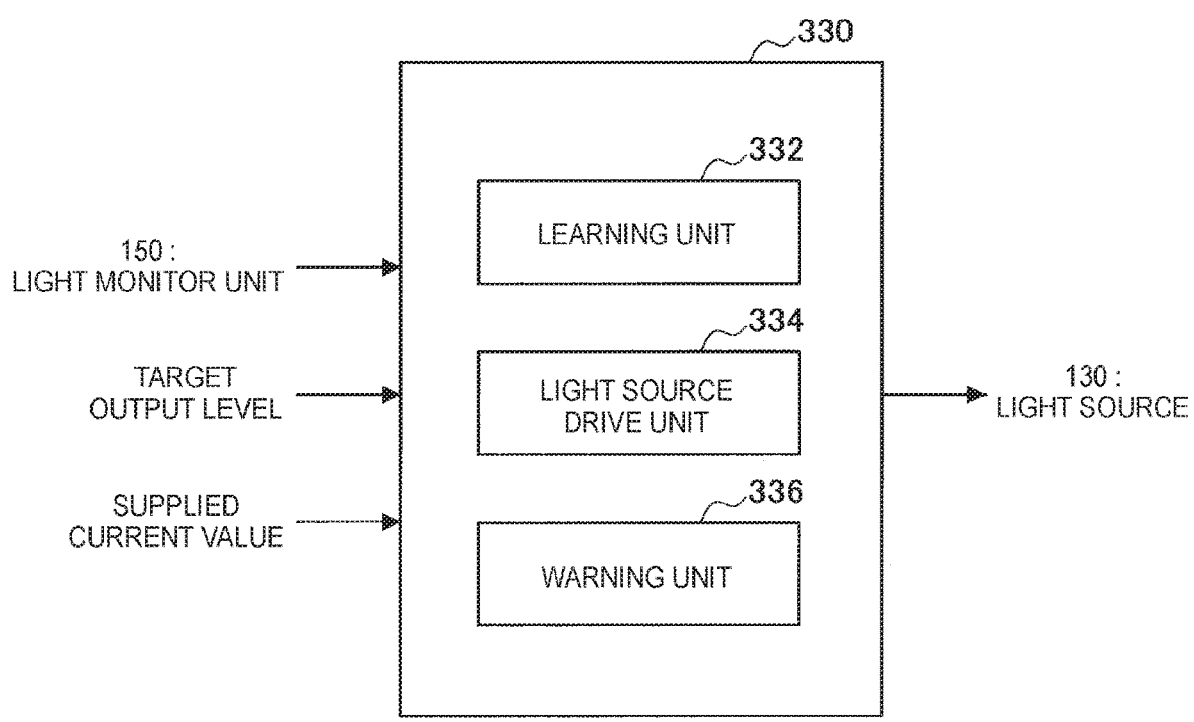
FIG. 3 is a block diagram illustrating a functional configuration of a control unit.

The light source device 300 according to the present embodiment includes a common control unit 330 that performs drive control of the red light source 130R, the green light source 130G, and the blue light source 130B. FIG. 3 is a block diagram illustrating a functional configuration of the control unit 330. The control unit 330 includes a learning unit 332, a light source drive unit 334, and a warning unit 336.

(Learning Unit)

The learning unit 332 learns target values $P''_R$, $P''_G$, and $P''_B$ of detection values $P_r$, $P_g$, and $P_b$ from the light monitor units 150 when illumination light is output from the light source device 300 at a selectable output level, for each of the red light source 130R, the green light source 130G, and the blue light source 130B. More specifically, with the light source device 300 according to the present embodiment, an output level of illumination light output from the light source device 300 can be set at a plurality of levels (1 to N). Also, a white balance of illumination light to be output is set beforehand, and output of the illumination light can be adjusted while maintaining the white balance, i.e., while maintaining the ratio of the light amounts of the lights of each of the colors of R, G, and B.

At the stage where the initial setting of the light source device 300 is performed, such as when the light source device 300 is shipped from a factory, the learning unit 332 causes the red light source 130R, the green light source 130G, and the blue light source 130B to be driven at all of the output levels (1 to N), and causes all detection values $P''_r$, $P''_g$, and $P''_b$ of the light monitor units 150 at that time to be stored. At this time, the detection values $P''_r$, $P''_g$, and $P''_b$ stored for each output level (1 to N) become the target values $P''_R$, $P''_G$, and $P''_B$ when each of the light sources 130 is driven by the light source drive unit 334.

Note that in a case where a user can adjust the white balance of the illumination light output from the light source device 300, the learning process described above may be performed when adjustment of the white balance is complete.

(Light Source Drive Unit)

The light source drive unit 334 performs drive control on the red light source 130R, the green light source 130G, and the blue light source 130B. In the present embodiment, the light source drive unit 334 sets a drive current $I_r$, $I_g$, and $I_b$ for each of the light sources 130 such that the detection values $P_r$, $P_g$, and $P_b$ detected by the light monitor units 150 come to match the predetermined target values $P''_R$, $P''_G$, and $P''_B$, for each of the light sources 130, and outputs a drive command to the light source drive circuit 310. In a state where each of the light sources 130 is not deteriorated, the light source drive unit 334 drives each of the light sources 130 on the basis of the target values $P''_R$, $P''_G$, and $P''_B$ corresponding to the output level (1 to N) set beforehand.

When setting the target values $P''_R$, $P''_G$, and $P''_B$ of the detection values $P_r$, $P_g$, and $P_b$ from the light monitor units 150, the light source drive unit 334 may use a correlation between a luminance value detected by a light receiving unit 230 of the imaging device 200 and the detection values $P_r$, $P_g$, and $P_b$ from the light monitor units 150. In this case, the light source drive unit 334 may calculate a calibration formula expressing the correlation between the detection values $P_r$, $P_g$, and $P_b$ from the light monitor units 150 and the luminance value detected by the light receiving unit 230 of the imaging device 200, for each of the red light, the green light, and the blue light, at the start of use of the imaging system 20 or at an appropriate timing.

An acquisition process of the correlation (calibration formula) is carried out, for example, by attaching a cover to the distal end of an endoscope probe, for example, such that a white subject as a reference is imaged. Aside from attaching a cover to the distal end of the endoscope probe, the correlation acquisition process may be performed while imaging a white subject determined beforehand. More specifically, the light source drive unit 334 causes red light to be emitted while changing the drive current supplied to the red light source 130R, in a state in which green light and blue light are not being emitted, for example. In this state, the light source drive unit 334 acquires a detection value Qr detected by the red light monitor unit 150R and the luminance value detected by the light receiving unit 230, for a plurality of drive current values. The light source drive unit 334 calculates a calibration formula expressing the correlation between the detection value Qr for red light and the luminance value, on the basis of a plurality of the acquired detection values Qr and luminance values. While a quadratic polynomial, for example, can be used for the calibration formula, the method of calculating the calibration formula, and the degree of the calibration formula can be set as appropriate.

The light source drive unit 334 also calculates calibration formulas expressing the correlation for the green light source and the blue light source by the same procedure. However, the order in which the calibration formulas are calculated is not particularly limited. The light source drive unit 334 can set the target values $P''_R$, $P''_G$, and $P''_B$ of the light amount of each light source so as to obtain a luminance value of the light of each color, which corresponds to the output level (1 to N) and the RGB ratio of illumination light, by obtaining the correlation between the luminance value and the detection value Pr from the light monitor units 150.

The light source drive unit 334 decreases the drive currents $I_r$, $I_g$, and $I_b$ in a case where the detection values $P_r$, $P_g$, and $P_b$ detected by the light monitor units 150 are greater than the target values $P''_R$, $P''_G$, and $P''_B$ and increases the drive currents $I_r$, $I_g$, and $I_b$ in a case where the detection values $P_r$, $P_g$, and $P_b$ are less than the target values $P''_R$, $P''_G$, and $P''_B$. At this time, the light amount decreases as deterioration of the light sources 130 progresses, so the drive currents $I_r$, $I_g$, and $I_b$ of the light sources 130 required to maintain the light amount of the emitted light at the same level are increased. Note that with the light source device 300, maximum current values (hereinafter, also referred to as "maximum drive currents") $I_R$, $I_G$, and $I_B$ that can be supplied to the light sources 130 are defined. These maximum drive currents $I_R$, $I_G$, and $I_B$ may be, for example, rated current values or arbitrarily set values.

(Warning Unit)

The warning unit 336 performs a primary warning to inform the user about deterioration of the light sources 130, when the drive currents $I_r$, $I_g$, and $I_b$ reach predetermined reference values. For example, the predetermined reference values may be the maximum drive currents $I_R$, $I_G$, and $I_B$ that can be supplied to the light sources 130. That is, the warning unit 336 performs the primary warning when the values of the drive currents $I_r$, $I_g$, and $I_b$ of the light sources 130, which are supplied such that the detection values $P_r$, $P_g$, and $P_b$ from the light monitor units 150 come to match the target values $P''_R$, $P''_G$, and $P''_B$, increase with the deterioration of the light sources 130 and reach the maximum drive currents $I_R$, $I_G$, and $I_B$.

Figure 4:
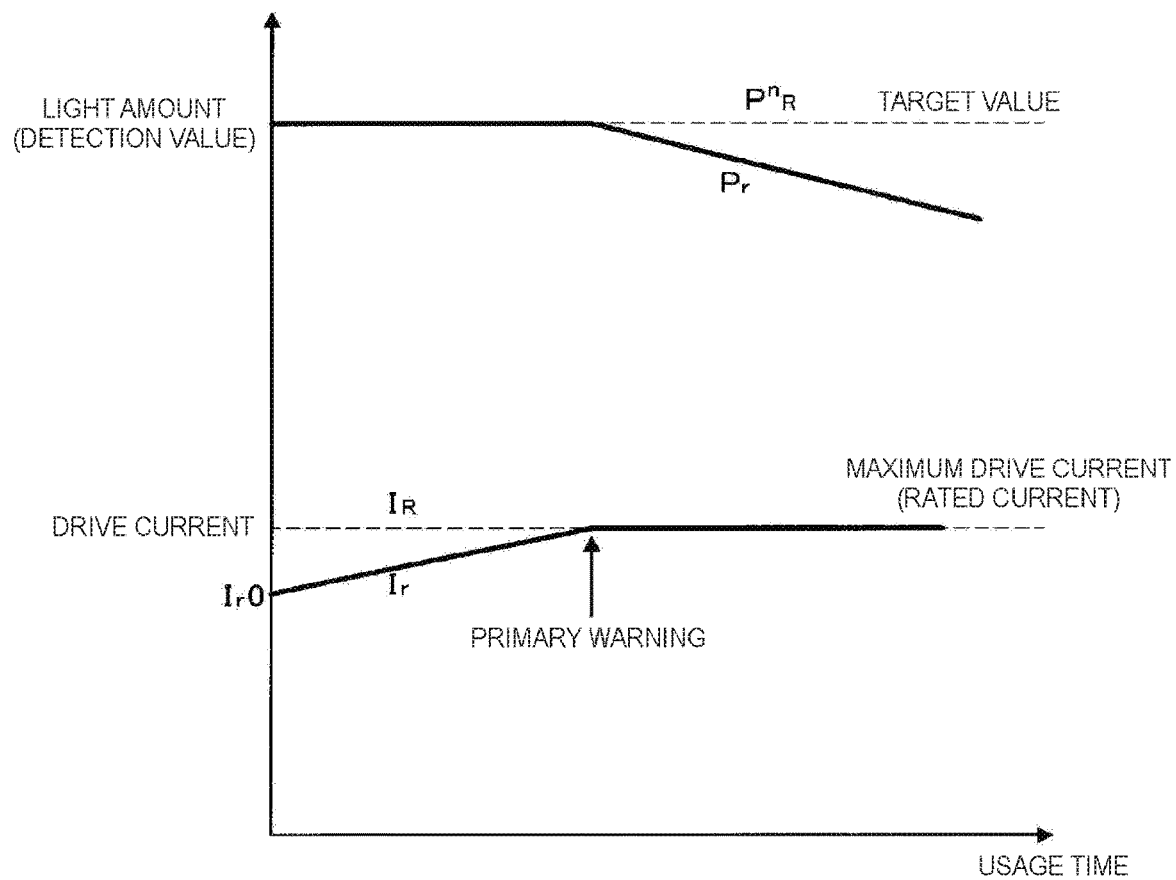
FIG. 4 is an explanatory view of a timing of a primary warning by a warning unit.

FIG. 4 is a view for illustrating the timing of the primary warning by the warning unit 336 and shows a change in the drive current $I_r$ and light amount (the detection value $P_r$ of the red light monitor unit 150R), in a case where the red light source 130R is driven such that the light amount of the emitted light comes to match the predetermined target value $P''_R$. For example, it will be assumed that the drive current $I_r$ when the detection value $P_r$ from the red light monitor unit 150R comes to match the target value $P''_R$ is $I_r0$ when the light source device 300 is shipped from a factory or after the red light source 130R is replaced. The drive current $I_r$ when the detection value $P_r$ from the red light monitor unit 150R matches the target value $P''_R$ gradually increases as deterioration progresses with the passages of usage time of the red light source 130R.

When the drive current $I_r$ reaches the maximum drive current $I_R$, the drive current $I_r$ is thereafter unable to be made to increase so the detection value $P_r$ from the red light monitor unit 150R gradually decreases. Because the rate at which deterioration progresses is different for each of the red light source 130R, the green light source 130G, and the blue light source 130B, the white balance of the illumination light will change if only the light amount from the red light source 130R decreases, for example. Therefore, the warning unit 336 urges the user to replace the red light source 130R by performing the primary warning at the time when the drive current $I_r$ of the red light source 130R reaches the maximum drive current $I_R$. The primary warning may be a warning by visual display, such as a warning display by characters or graphics or the like, or a warning by sound, such as the generation of a warning sound, for example, but is not limited to these examples.

Figure 5:
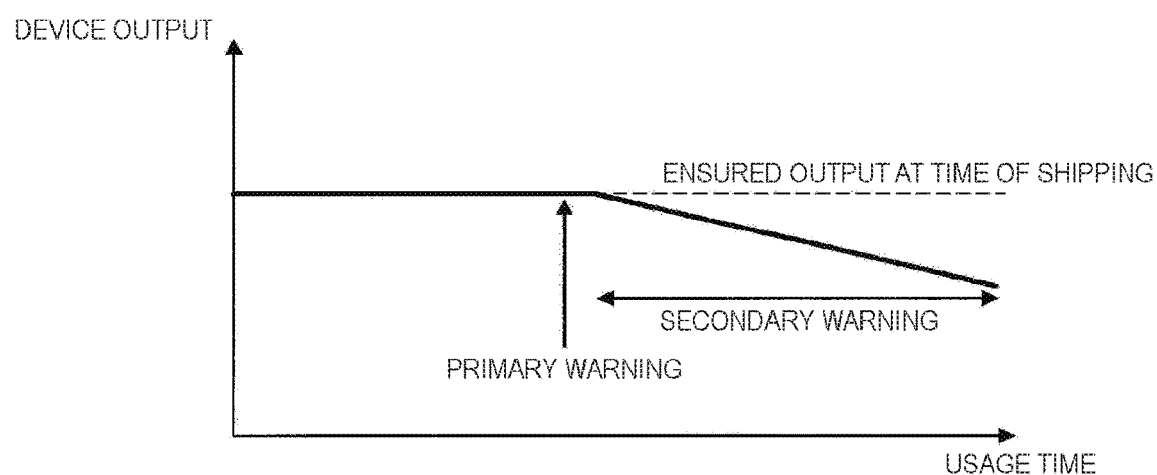
FIG. 5 is an explanatory view of a timing of a secondary warning by a warning unit.

Also, the warning unit 336 performs a predetermined process on the basis of the deterioration of the light sources 130, after the primary warning is performed. FIG. 5 is a view for illustrating the timing at which the predetermined process after the primary warning is performed and shows a change in output of the light source device 300. After one of the light sources 130 from among the red light source 130R, the green light source 130G, and the blue light source 130B deteriorates and the primary warning is performed, the light amount will gradually decrease even though the maximum drive current continues to be supplied to the deteriorated light source 130. Accordingly, the light source drive unit 334 causes the target output level of the illumination light to gradually decrease while maintaining the white balance of the illumination light. Also, the warning unit 336 performs a predetermined process in accordance with the deterioration level of the light source 130, after the primary warning is performed.

Here, in the present specification, the deterioration level of the light source is a value set in accordance with the degree of decrease in a maximum light amount actually able to be output, with respect to an initial value of the maximum light amount (for example, the light amount output at the maximum rated current of a light emitting element) of the light source.

Although the user is urged by the primary warning to replace the light source 130, it is conceivable that it may not be possible to stop the light source device 300 if it is during surgery, for example, and it is also conceivable that the light source 130 may not be able to be replaced immediately. Therefore, the warning unit 336 performs a predetermined process in accordance with the deterioration of the light source 130, in a case where the light source 130 continues to be used.

For example, the warning unit 336 may perform a secondary warning for informing the user of the deterioration level of the light source 130. The secondary warning may be a warning by visual display, or a warning by sound, for example. In a case where the secondary warning is a warning by visual display, the warning unit 336 may change the color or brightness of the warning display, the reading of a level meter, or the blinking interval of the warning display or the like, in accordance with the deterioration level of the light source 130, for example. Alternatively, the warning unit 336 may directly display the deterioration level with characters or the like. Also, in a case where the secondary warning is a warning by sound, the warning unit 336 may change the loudness or interval of the warning sound, or the type of sound or the like, in accordance with the deterioration level of the light source 130.

Also, the warning unit 336 may prohibit the driving of the light source 130 beyond a predetermined output, in accordance with the deterioration level of the light source 130, after the primary warning is performed. More specifically, in a case where one of the light sources 130 from among the red light source 130R, the green light source 130G, and the blue light source 130B has deteriorated, the warning unit 336 may limit the maximum value of the output level (1 to N) that can be set, in accordance with the deterioration level of the deteriorated light source 130. For example, the state in which the primary warning is performed is a state in which it is difficult for a portion of the light sources 130 to output emitted light of a desired light amount at the current target output level (1 to N), so the warning unit 336 may reduce the target output level (1 to N) one level. As a result, when drive control of each of the light sources 130 is performed by the light source drive unit 334, only the light amount of a portion of the light sources 130 is reduced, thus enabling a change in the white balance to be avoided.

1-1-6. Operating Panel

The operating panel 400 may function as an input unit that receives operation input of the light source device 300 by the user, and function as a display unit that displays the state and the like of the light source device 300. For example, the operating panel 400 may be formed by a touch panel.

Figure 6:
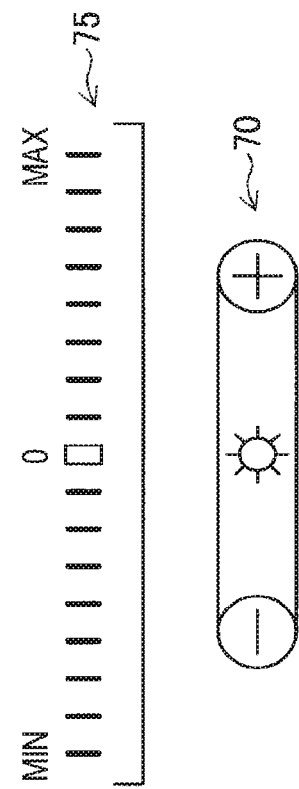
FIG. 6 is a schematic view of an example of an operating panel of a light source device.
Figure 6:
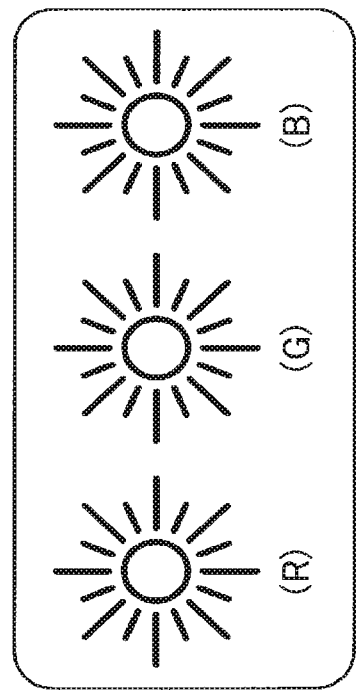

FIG. 6 illustrates one example of a portion for adjusting the output level of illumination light and a portion for displaying the deterioration level of the light source, of the operating panel 400. The operating panel 400 is provided with an output level operation input portion 70, an output level display portion 75, and a deterioration level display portion 80. The user can cause the target output level of illumination light to increase or decrease by touch operating a plus button or a minus button of the output level operation input portion 70. The current output level is displayed on the output level display portion 75. In the example illustrated in FIG. 6, the target output level of the illumination light is able to be set at 17 levels. In a case where the target output level of the illumination light is adjusted automatically, the current output level may be displayed on the output level display portion 75. The deterioration level display portion 80 displays the deterioration level of each of the light sources 130, thereby informing the user.

1-2. Configuration Example of Imaging Device

The imaging device 200 includes an optical system 210, a light receiving unit 230, and an image processing unit 250. The optical system 210 takes in illumination light irradiated from the light source device 300 and the reflected light. In the case of the endoscopic device according to the present embodiment, the optical system 210 may take in the illumination light and the reflected light via an observation window provided at the distal end of the endoscopic probe.

The light receiving unit 230 is formed by a solid-state imaging element such as charge coupled device (CCD) or a complementary metal oxide semiconductor (CMOS), for example. The light receiving unit 230 is arranged at an imaging position of the optical system 210, and a subject image in which a target site is imaged is captured by illumination light being irradiated on the target site and reflected (radiated light). The light receiving unit 230 generates an image signal by photoelectrically converting the captured subject image and outputting the generated image signal to the image processing unit 250.

The image processing unit 250 is formed by a CPU and a storage element, and generates an image on the basis of the image signal output from the light receiving unit 230, and causes a monitor or the like, not illustrated, to display the image. At this time, the image processing unit 250 may detect the luminance of each pixel in the entire image or in a predetermined region, and further, calculate the average value of the luminance detected for each pixel, and output the calculated average value of the luminance to the control unit 330 of the light source device 300. Information regarding the output luminance may be used in the control of each of the light sources 130.

2. Control Process of Light Source Device

Heretofore, an overall configuration example of the imaging system 20 according to the present embodiment has been described. Next, a control process of the light source device 300 of the imaging system 20 according to the present embodiment will be described.

2-1. Outline of Control Process

Figure 7:
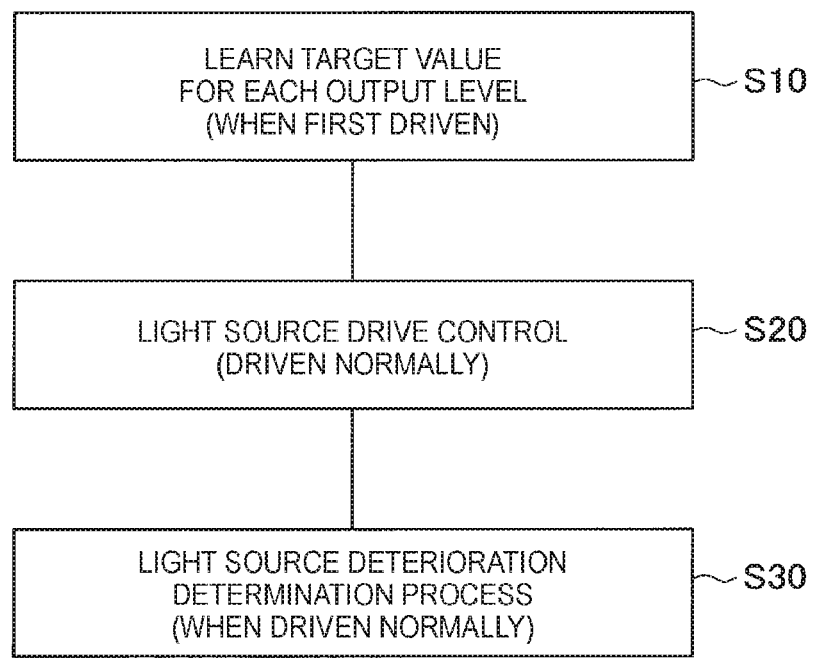
FIG. 7 is a flowchart illustrating an outline of a control process by a control unit.

First, an outline of the control process of the light source device 300 will be described. FIG. 7 schematically illustrates the flow of the control process of the light source device 300. The control unit 330 of the light source device 300 performs a process of learning the detection values $P''_r$, $P''_g$, and $P''_b$ from the light monitor units 150 in a case where illumination light is caused to be output at all of the output levels (1 to N) when the light source device 300 is first driven such as when the light source device 300 is shipped from the factory, for example (step S10). The obtained detection values $P''_r$, $P''_g$, and $P''_b$ of the light monitor units 150 are stored in a storage unit, not illustrated. At this time, the relationship between the light amount and the value of drive current other than the current value actually supplied may be obtained by performing interpolation processing or obtaining an approximation formula. As a result, when driven normally, the target values $P''_R$, $P''_G$, and $P''_B$ when each of the light sources 130 is made to be driven are set in accordance with the selected target output level (1 to N).

When the target values $P''R$, $P''_G$, and $P''_B$ of the detection values $P_r$, $P_g$, and $P_b$ from the light monitor units 150 are obtained for each output level (1 to N), the control unit 330 of the light source device 300 performs drive control of each of the light sources 130 such that the light amount of the emitted light of each of the light sources 130 becomes a desired light amount, in accordance with the selected target output level (1 to N), when the imaging system 20 is used (step S20). With the light source device 300 according to the present embodiment, the target values $P''_R$, $P''_G$, and $P''_B$ of the detection values $P_r$, $P_g$, and $P_b$ from the red light monitor unit 150R, the green light monitor unit 150G, and the blue light monitor unit 150B are specified in accordance with the target output level (1 to N) selected by the user or the like. The control unit 330 controls the drive currents $I_r$, $I_g$, and $I_b$ to each of the light sources 130 on the basis of the specified target values $P''_R$, $P''_G$, and $P''_B$.

While the drive control of each of the light sources 130 is performed, the control unit 330 performs a deterioration determination process for each of the light sources 130 (step S30). The deterioration determination process includes a process of performing the primary warning, and a process that is performed in accordance with the deterioration level of the light source 130 after performing the primary warning. According to this deterioration determination process, the user is able to recognize that deterioration of one of the light sources 130 is progressing and know the need for replacement.

2-2. Target Value Learning Process

Figure 8:
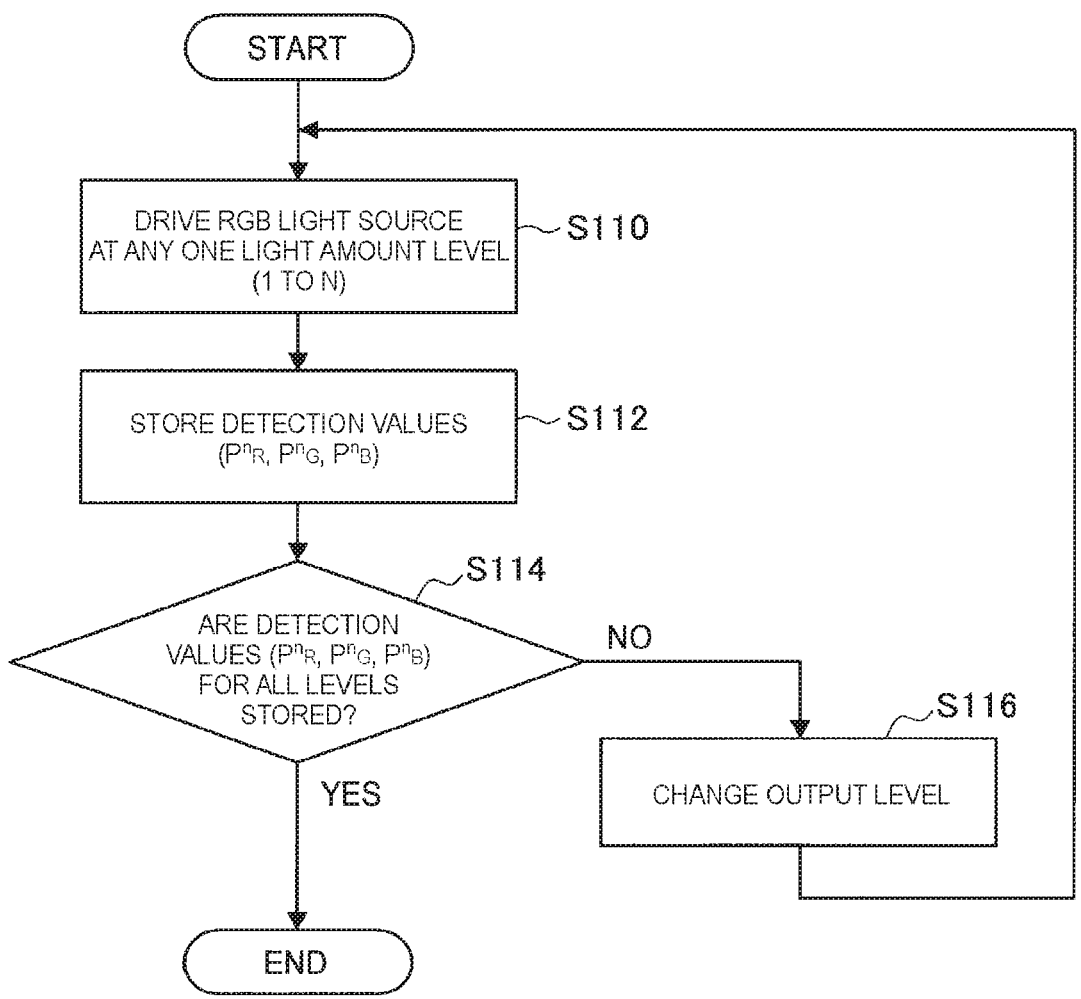
FIG. 8 is a flowchart illustrating an example of a target value learning process by a learning unit.

FIG. 8 is a flowchart illustrating an example of a target value learning process. In step S110, the learning unit 332 of the control unit 330 causes the red light source 130R, the green light source 130G, and the blue light source 130B to be driven at one of the selectable output levels (1 to N). Next, in step S112, the learning unit 332 causes the detection values $P''_r$, $P''_g$, and $P''_b$ from the red light monitor unit 150R, the green light monitor unit 150G, and the blue light monitor unit 150B to be stored as the target values $P''_R$, $P''_G$, and $P''_B$.

Next, in step S114, the learning unit 332 determines whether the target values $P''_R$, $P''_G$, and $P''_B$ of the detection values $P''_r$, $P''_g$, and $P''_b$ from the light monitor units 150 at all of the output levels (1 to N) have been stored. If there is an output level (1 to N) for which the target values $P''_R$, $P''_G$, and $P''_B$ have not been stored (S114: No), the process proceeds on to step S116 and the learning unit 332 changes the output level to the output level for which the target values $P''_R$, $P''_G$, and $P''_B$ have not been stored, and then returns to step S110. The order of the output levels for which the target values $P''_R$, $P''_G$, and $P''_B$ are learned is not limited. The output levels may gradually increase from a minimum value or may gradually decrease from a maximum value. Alternatively, the output levels may be made to change at random.

If the target values $P''_R$, $P''_G$, and $P''_B$ have been stored for all of the output levels (1 to N) (S114: Yes), the learning unit 332 ends the target value learning process.

2-3. Light Source Driving Process

Figure 9:
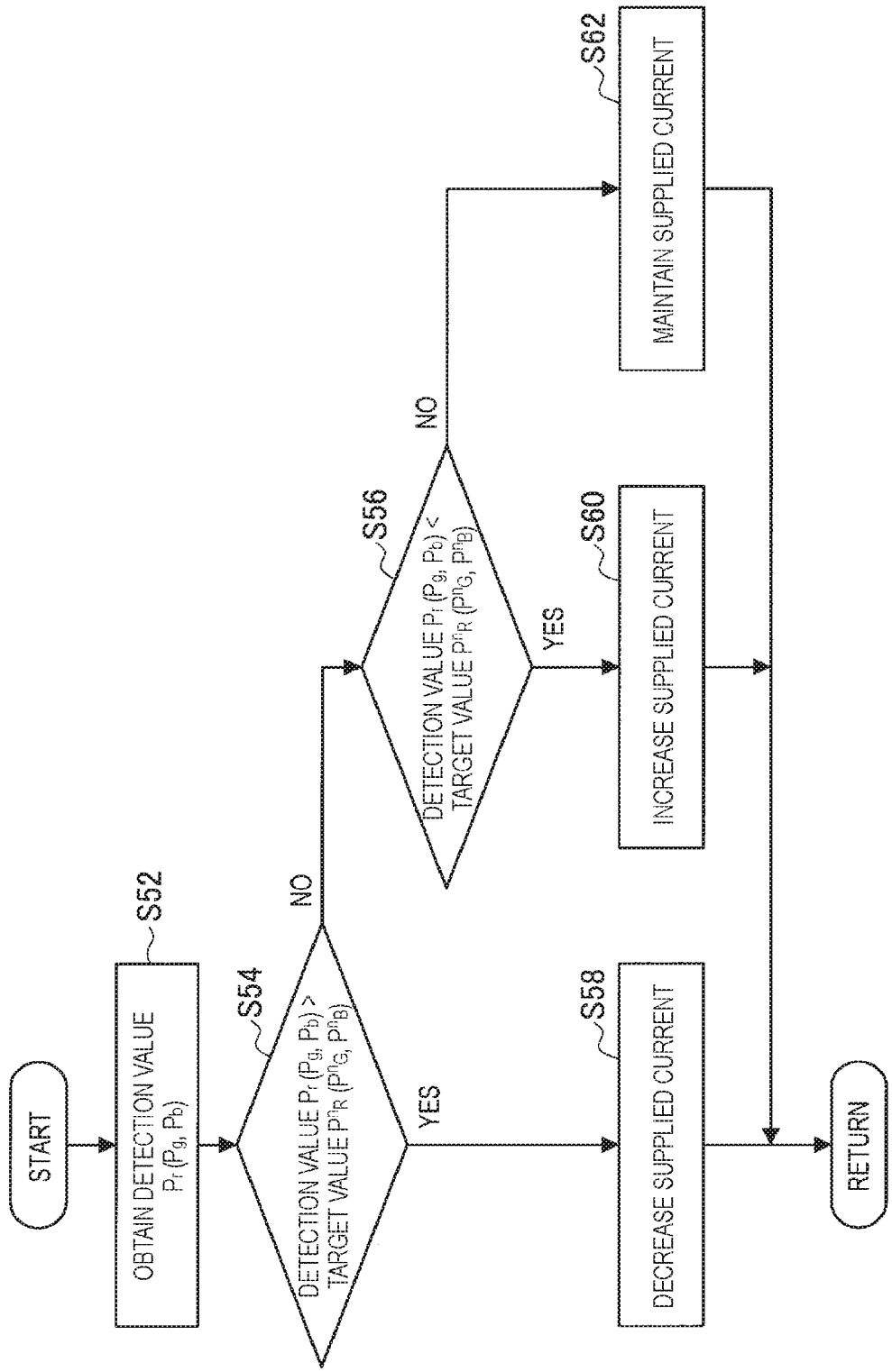
FIG. 9 is a flowchart illustrating an example of a light source drive control process by a light source drive unit.

FIG. 9 is a flowchart illustrating an example of a driving process for the light sources 130. The light source drive unit 334 detects the detection value $P_r$ ($P_g$, $P_b$) from the light monitor unit 150R (150G, 150B) for each of the light sources 130 in step S52, and determines whether the detection value $P_r$ ($P_g$, $P_b$) is greater than the target value $P''_R$ ($P''_G$, $P''_B$) corresponding to the currently selected target output level (1 to N) in step S54. In a state in which none of the light sources 130 are deteriorated, the target value $P''_R$ ($R''_G$, $P''_B$) initially set for the selected target output level (1 to N) is compared to the detection value $P_r$ ($P_g$, $P_b$). However, if one of the light sources 130 from among the red light source 130R, the green light source 130G, and the blue light source 130B is deteriorated, the upper limits of the target values $P''_R$, $P''_G$, and $P''_B$ of all of the light sources 130 are limited in accordance with the light amount of the emitted light that is able to be output from the deteriorated light source 130.

If the detection value $P_r$ ($P_g$, $P_b$) is greater than the current target value $P''_R$ ($P''_G$, $P''_B$) (S54: Yes), the light source drive unit 334 proceeds on to step S58 and causes the drive currents $I_r$, $I_g$, and $I_b$ of the light source 130R (130G, 130B) to decrease. If, on the other hand, the detection value $P_r$ ($P_g$, $P_b$) is equal to or less than the current target value $P''_R$ ($P''_G$, $P''_B$) (S54: No), the light source drive unit 334 proceeds on to step S56 and determines whether the detection value $P_r$ ($P_g$, $P_b$) is less than the current target value $P''_R$ ($P''_G$, $P''_B$). If the detection value $P_r$ ($P_g$, $P_b$) is less than the current target value $P''_R$ ($P''_G$, $P''_B$) (S56: Yes), the light source drive unit 334 proceeds on to step S60 and causes the drive currents $I_r$, $I_g$, and $I_b$ of the light source 130R (130G, 130B) to increase. If, on the other hand, the detection value $P_r$ ($P_g$, $P_b$) is equal to the current target value $P''_R$ ($P''_G$, $P''_B$) (S56: No), the light source drive unit 334 proceeds on to step S62 and causes the drive currents $I_r$, $I_g$, and $I_b$ to be maintained.

The light source drive unit 334 repeats step S52 to step S62 described above for each of the red light source 130R, the green light source 130G, and the blue light source 130B, and controls the drive currents $I_r$, $I_g$, and $I_b$ of each of the light sources 130 such that the detection value $P_r$ ($P_g$, $P_b$) comes to match the target value $P''_R$ ($P''_G$, $P''_B$). In a case where deterioration of the light source 130 progresses, the detection value $P_r$ ($P_g$, $P_b$) will be less than the current target value $P''_R$ ($P''_G$, $P''_B$), so the routine described above is repeated while the drive currents $I_r$, $I_g$, and $I_b$ are gradually increased in step S60.

2-4. Deterioration Determination Process

Figure 10:
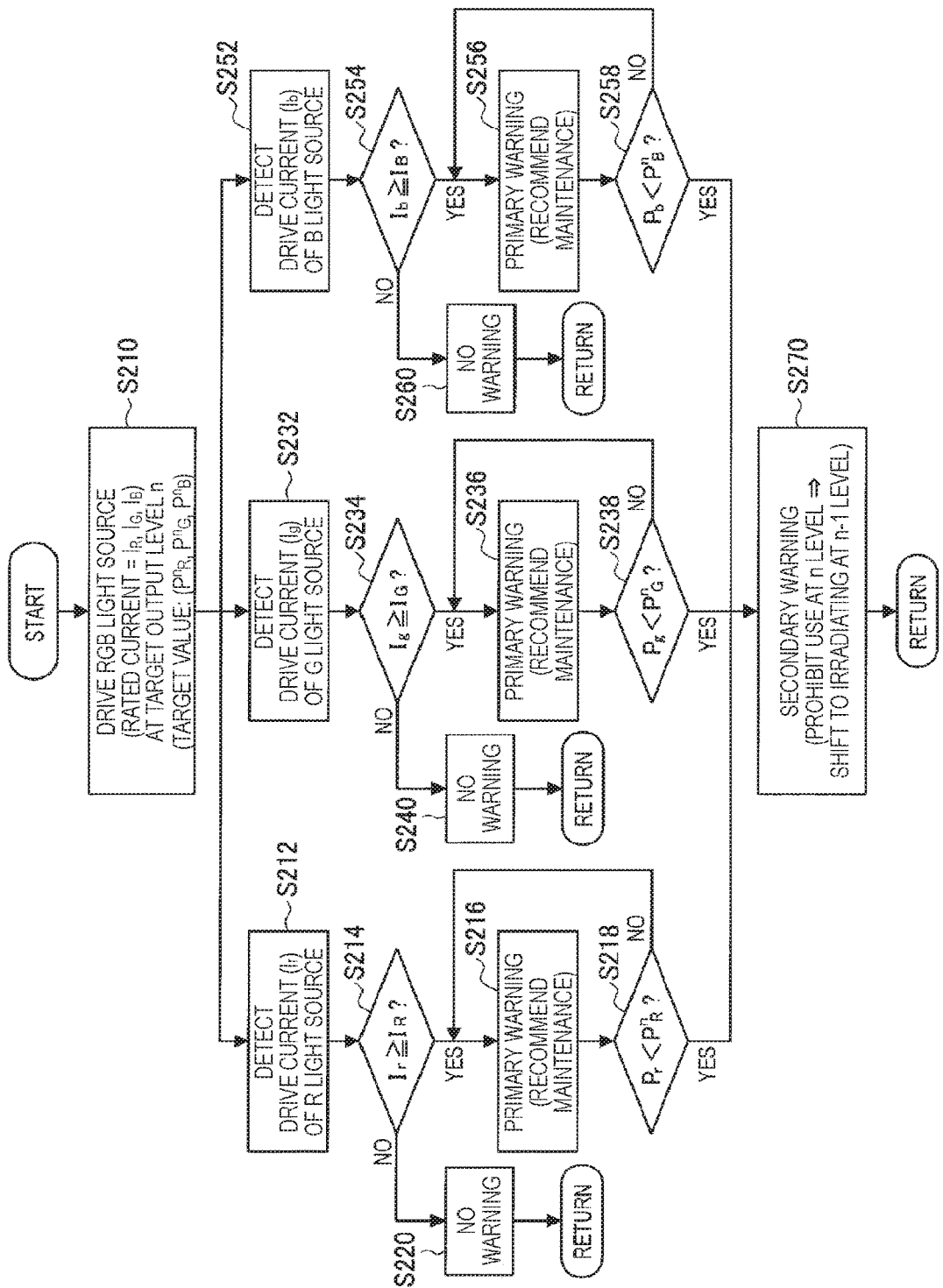
FIG. 10 is a flowchart illustrating an example of a light source deterioration determination process by a warning unit.

FIG. 10 is a flowchart illustrating an example of a deterioration determination process for the light sources 130. First, in step S210, the light source drive unit 334 of the control unit 330 causes each of the light sources 130 to be driven at the target values $P''_R$, $P''_G$, and $P''_B$ corresponding to a currently selected target output level n. Note that the maximum drive currents $I_R$, $I_G$, and $I_B$ that can be supplied to each of the light sources 130 are assumed to be rated currents.

Next, the warning unit 336 performs a deterioration determination for each of the red light source 130R, the green light source 130G, and the blue light source 130B. More specifically, in step S212, the warning unit 336 detects the drive current $I_r$ being supplied to the red light source 130R. Next, the warning unit 336 determines whether the detected drive current $I_r$ has reached the rated current $I_R$. If the drive current $I_r$ is less than the rated current $I_R$ (S214: No), it can be determined that the red light source 130R is not deteriorated, so the warning unit 336 proceeds on to step S220 and determines that a warning is not to be issued, and then returns to step S210.

If, on the other hand, it is determined in step S214 that the detected drive current $I_r$ has reached the rated current $I_R$ (S214: Yes), the warning unit 336 proceeds on to step S216 and performs the primary warning. For example, the warning unit 336 may perform the warning display by characters or graphics or the like or may issue a warning sound. The warning method is not limited to these examples. Consequently, the user is urged to replace the red light source 130R. Next, in step S218, the warning unit 336 determines whether the detection value $P_r$ from the red light monitor unit 150R is below the current target value $P''_R$. If the detection value $P_r$ is equal to or greater than the target value $P''_R$ (S218: No), the warning unit 336 returns to step S216 and repeats comparing the detection value $P_r$ to the target value $P''_R$ while continuing the primary warning. If, on the other hand, the detection value $P_r$ is below the target value $P''_R$ (S218: Yes), the warning unit 336 proceeds on to step S270.

For the green light source HOG and the blue light source 130B as well, step S232 to step S240, and step S252 to step S260 are performed, similar to step S212 to step S218 described thus far. Accordingly, if one of the light sources 130 from among the red light source 130R, the green light source 130G, and the blue light source 130B deteriorates, and the detection values $P_r$, $P_g$, and $P_b$ from the light monitor units 150 are below the target values $P''_R$, $P''_G$, and $P''_B$, the process proceeds on to step S270.

In step S270, the warning unit 336 performs the secondary warning according to the deterioration level of the deteriorated light source 130. For example, the warning unit 336 may change the color, brightness, or blinking interval or the like of the warning display, or change the reading of a level meter, in accordance with the deterioration level of the deteriorated light source 130. Also, the warning unit 336 may change the loudness, generation interval, or type of the warning sound in accordance with the deterioration level of the deteriorated light source 130. The warning method is not limited to these examples.

Also, in step S270, the warning unit 336 prohibits the use of the light source device 300 at the currently selected target output level n and causes the output to change to output at an output level n−1 that is one level lower. That is, in a state in which one of the light sources 130 is deteriorated, even if the light source device 300 continues to be driven while maintaining the output level n, the light source 130 is unable to be made to drive at a light amount $P''$ corresponding to the current target output level n, so the output of the illumination light will decrease, and the white balance will also change. Therefore, the warning unit 336 causes the target output level to decrease and thus causes the output of the illumination light to decrease while maintaining the white balance. Then, the process returns to step S210, the target output level is set to n−1, and step S210 to step S270 described thus far are repeated.

3. Examples of Warning Process

Next, specific examples of the primary warning and the secondary warning performed by the warning unit 336 of the control unit 330 will be described.

3-1. Example in Which Warning Display is Performed for Each Light Source

Figure 11:
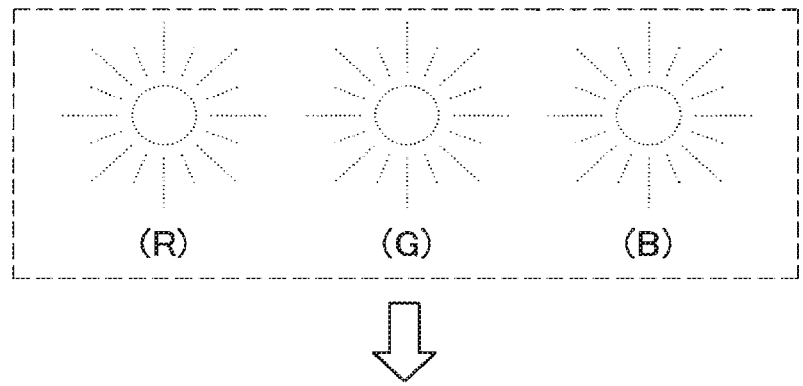
FIG. 11 is an explanatory view of an example in which a warning display is performed for each light source.
Figure 11:
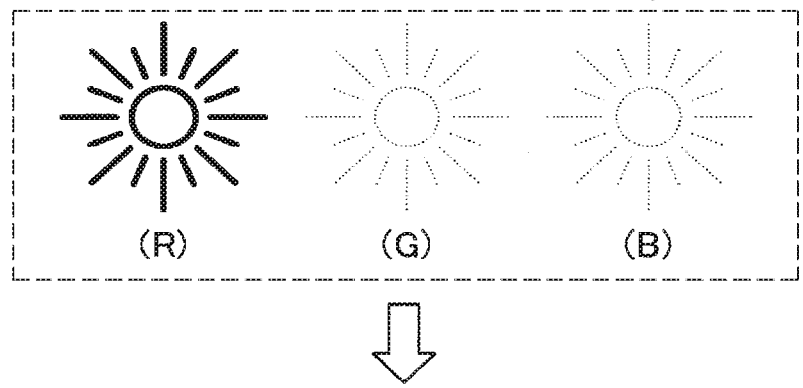
Figure 11:
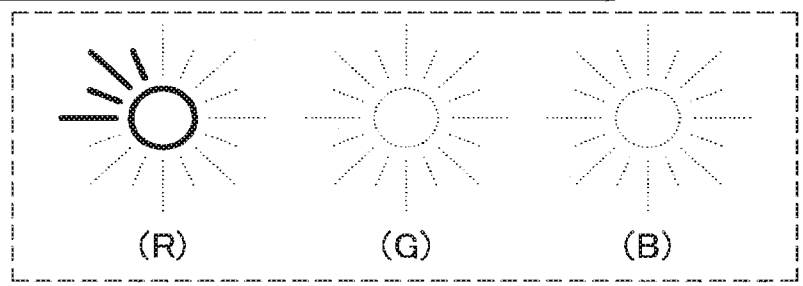

As illustrated in FIG. 6, the operating panel 400 of the light source device 300 according to the present embodiment includes the deterioration level display portion 80 that performs a warning display for each of the red light source 130R, the green light source 130G, and the blue light source 130B. FIG. 11 is an explanatory view illustrating an example of a warning display displayed on the deterioration level display portion 80. The deterioration level display portion 80 has a warning display portion corresponding to each of the red light source 130R, the green light source 130G, and the blue light source 130B. Each warning display portion is formed by a circle in the center and 16 linear portions that extend in a radial fashion around the circle. In a normal state in which none of the light sources are deteriorated, none of the warning displays are illuminated.

Here, it will be assumed that the red light source 130R has deteriorated and the drive current $I_r$ has reached the maximum drive current $I_R$, for example. Therefore, all of the warning display portions corresponding to the red light source 130R are illuminated. As a result, the user is able to know that the red light source 130R has deteriorated. Also, in a case where the deterioration of the red light source 130R has progressed further, the number of illuminated warning display portions corresponding to the red light source 130R is reduced by one in accordance with the deterioration level. In the example illustrated in FIG. 11, the deterioration level of the light source 130 is displayed with 17 levels, so the user is able to know that the red light source 130R is only able to output a level 5 light amount.

The warning display portions corresponding to each of the red light source 130R, the green light source 130G, and the blue light source 130B may be displayed in red, green, and blue, respectively, or markings may be provided that indicate which warning display portion corresponds to which light source 130, such as R, G, and B. The example in which a warning display is performed for each light source 130 is particularly advantageous in the case of the light source device 300 in which the light sources 130 can be replaced individually. Note that the mode of the warning display is not limited to the example described above and can be modified in a variety of ways.

Figure 12:
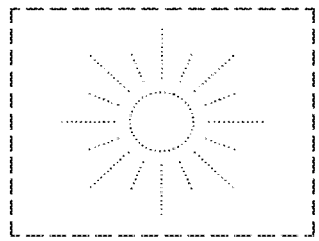
FIG. 12 is an explanatory view of an example in which a warning display is performed for a light source device as a whole.
Figure 12:
Figure 12:
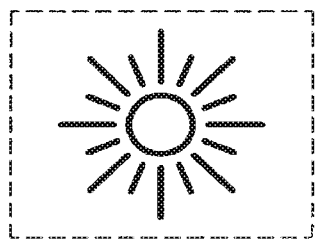
Figure 12:
Figure 12:
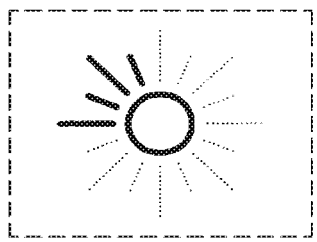

3-2. Example in Which Warning Display is Performed for Light Source Device as a Whole The warning display may be performed for the light source device 300 as a whole, instead of being performed for each of the red light source 130R, the green light source 130G, and the blue light source 130B. FIG. 12 is an explanatory view of an example in which a warning display is performed for the light source device 300 as a whole. In the example illustrated in FIG. 11, three warning display portions are provided, but in the example illustrated in FIG. 12, one warning display portion is provided. This warning display portion is not illuminated in a normal state in which none of the light sources are deteriorated.

Here, it will be assumed that the red light source 130R has deteriorated and the drive current $I_r$ has reached the maximum drive current $I_R$. In this case, the warning unit 336 described above limits the upper limit of the output level of the light source device 300, so the output of the illumination light is also made to decrease as the light amount of the red light source 130R decreases. Therefore, in the example illustrated in FIG. 12, all of the warning display portion is illuminated. The user is not able to identify the deteriorated light source 130, but in any case, is able to know that the output of the light source device 300 is reduced. Also, in a case where the deterioration of the red light source 130R has progressed further, the number of illuminated warning display portions is reduced by one in accordance with the deterioration level. Therefore, the user is able to know that the output of the light source device 300 is limited to level 5 or lower.

The example in which a warning display is performed for the light source device 300 as a whole is particularly advantageous in the case of the light source device 300 in which the red light source 130R, the green light source 130G, and the blue light source 130B are formed as a light source unit, and the unit as a whole can be replaced. Note that the mode of the warning display is not limited to the example described above and can be modified in a variety of ways.

Alternatively, in the example illustrated in FIG. 12, even if the user is not shown which light source 130 has deteriorated, an information log regarding the deteriorated light source 130 may be stored in a storage unit. As a result, a person who performs the work of replacing the light source 130 is able to know the deteriorated light source 130 and can also replace the light source 130 individually.

4. Conclusion

As described above, with the light source device 300 and the imaging system 20 according to the present embodiment, the light amounts of the light emitted from the light sources 130 are detected by the light monitor units 150, and the drive currents $I_r$, $I_g$, and $I_b$ of the light sources 130 are controlled such that the detection values $P_r$, $P_g$, and $P_b$ come to match the target values $P''_R$, $P''_G$, and $P''_B$. Also, when the drive currents $I_r$, $I_g$, and $I_b$ reach the maximum drive currents $I_R$, $I_G$, and $I_B$, the primary warning is performed and the user is urged to replace the light sources 130. Also, after the primary warning is performed, the upper limit of the output level of the illumination light to be output from the light source device 300 is limited in accordance to the maximum output of the deteriorated light source 130. Furthermore, after the primary warning is performed, the secondary warning is performed in accordance with the deterioration level of the light source 130, and the user is informed of the light amount level that can be output. Therefore, according to the light source device 300 and the imaging system 20 according to the present embodiment, it is possible to accurately determine the deterioration state of the light sources 130 on the basis of the actual usage environment or use period or the like of the light sources 130 and issue a warning to the user. As a result, the user is able to accurately grasp the replacement timing of the light sources.

Also, with the light source device 300 and the imaging system 20 according to the present embodiment, the upper limit of the output level of the light source device 300 as a whole is limited when one of the light sources 130 from among the red light source 130R, the green light source 130G, and the blue light source 130B has deteriorated. Therefore, even though the output of illumination light decreases, the ratio of light amounts of the lights of each color of R, G, and B, i.e., the white balance of the illumination light, is maintained, so surgery is able to be continued, for example.

5. Modified Examples

Heretofore, an example of the light source device 300 and the imaging system 20 according to the present embodiment has been described, but the light source device can be modified in a variety of ways. Several modified examples of the light source device will be described below.

5-1. First Modified Example

Figure 13:
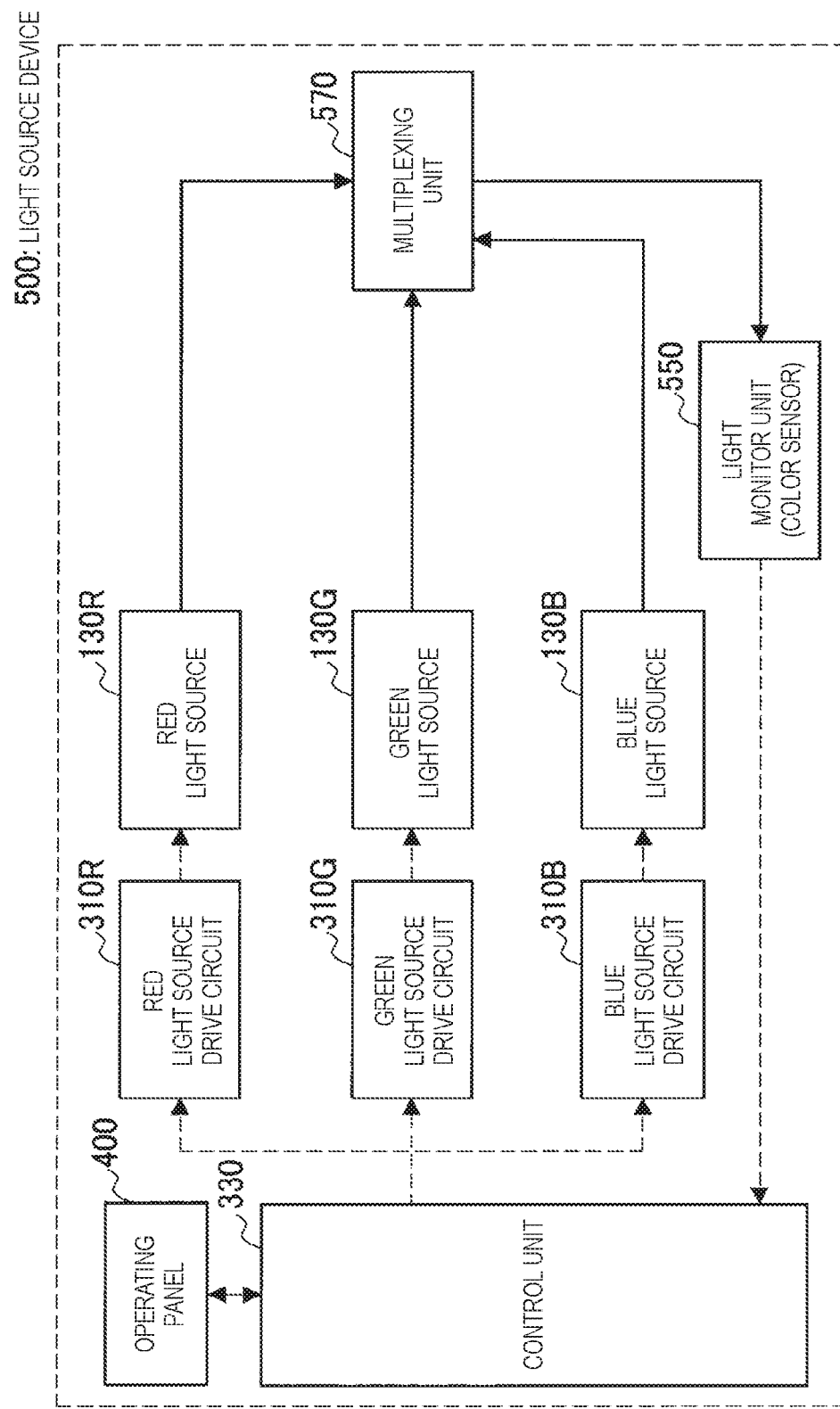
FIG. 13 is a block diagram illustrating an imaging system according to a first modified example.

FIG. 13 is block diagram illustrating a configuration example of a light source device 500 according to a first modified example. The light source device 500 according to the first modified example differs from the light source device 300 according to the embodiment described above in that one light monitor unit (color sensor) 550 detects the light amount of emitted light emitted from each of a plurality of light sources.

The light source device 500 includes a red light source 130R, a green light source 130G, a blue light source 130B, a red light source drive circuit 310R, a green light source drive circuit 310G, a blue light source drive circuit 310B, and a multiplexing unit 570. Also, the light source device 500 includes the color sensor 550 as the one light monitor unit. The red light source 130R, the green light source 130G, and the blue light source 130B can be configured similar to the light sources 130 of the light source device 300 according to the embodiment described above.

Figure 14:
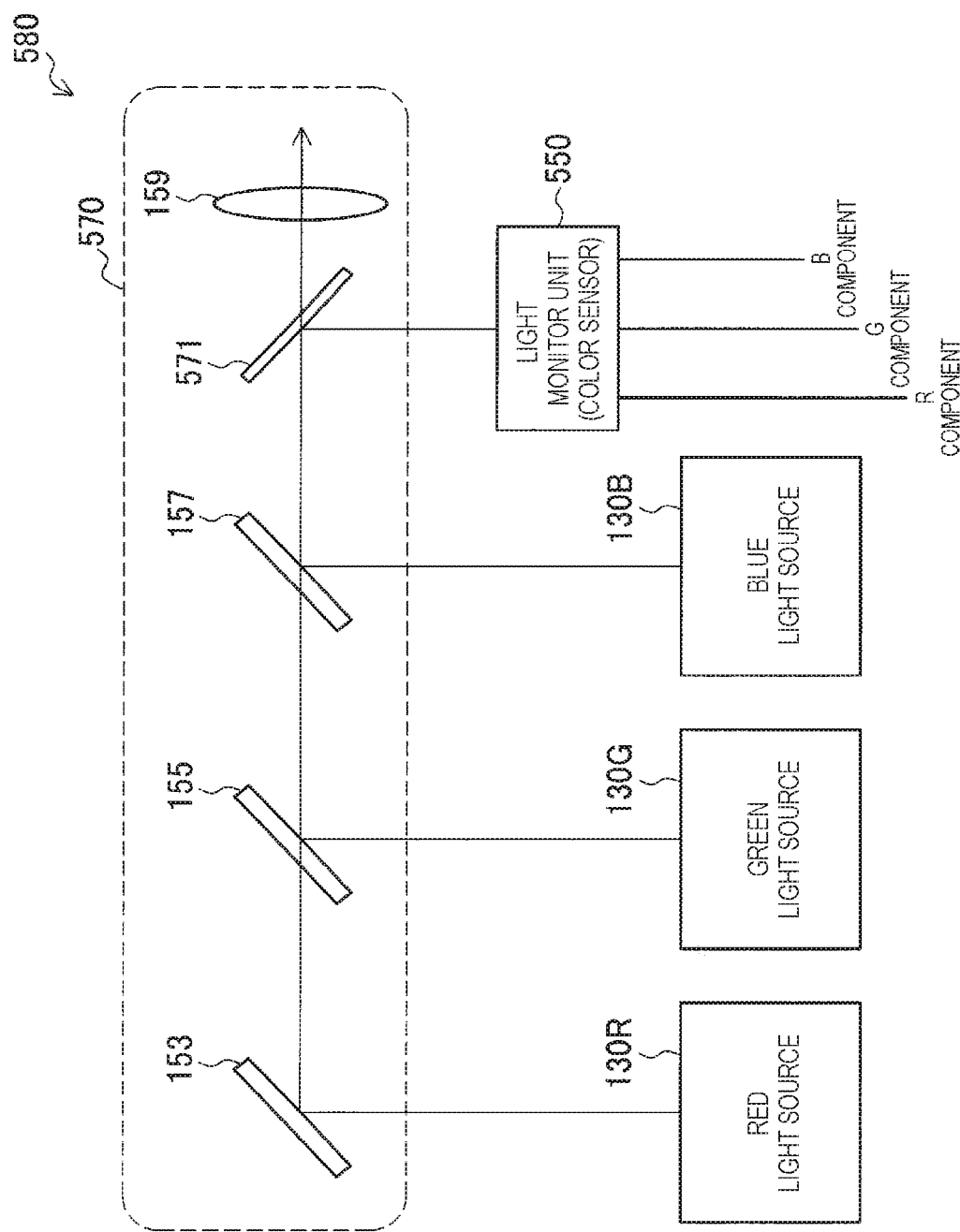
FIG. 14 is a schematic diagram illustrating an RGB multiplexing module having a light monitor unit (color sensor) according to the first modified example.

The multiplexing unit 570 multiplexes light of each color of R, G, and B, and emits the multiplexed light as illumination light. FIG. 14 is a schematic diagram illustrating a configuration example of a multiplexing module 580 that includes the multiplexing unit 570 and is provided with the color sensor 550. The multiplexing unit 570 of the light source device 500 includes a dichroic mirror 571 that reflects a portion of the multiplexed light and causes the path of the reflected portion of multiplexed light to change toward the color sensor 550. With this multiplexing module 580, the light amount of the light emitted from each of the light sources 130 is not detected by an individual light monitor unit. Instead, the multiplexed light is input into the color sensor 550, and the light amounts of the individual lights are detected by the color sensor 550. The color sensor 550 that is used is not particularly limited. A well-known color sensor can be used.

With the color sensor 550, light of a wavelength in the infrared region is cut from the incident light and dispersed into light of wavelengths of each of blue light, green light, and blue light, and the light amount of the light of each color is detected. The light amount of the light of each color detected by the color sensor 550 is converted into a voltage signal, respectively, and transmitted to the control unit 330. The control unit 330 can basically be configured similar to the control unit 330 of the light source device 300 according to the embodiment described above.

The light source device 500 according to the first modified example can detect the light amount of the emitted light emitted from each of the light sources 130 with the one color sensor (light monitor unit) 550, and execute each control process exemplified with the light source device 300 according to the embodiment described above. Therefore, according to the light source device 500 according to the first modified example, effects similar to the effects obtained by the light source device 300 according to the embodiment described above can be obtained.

5-2. Second Modified Example

Figure 15:
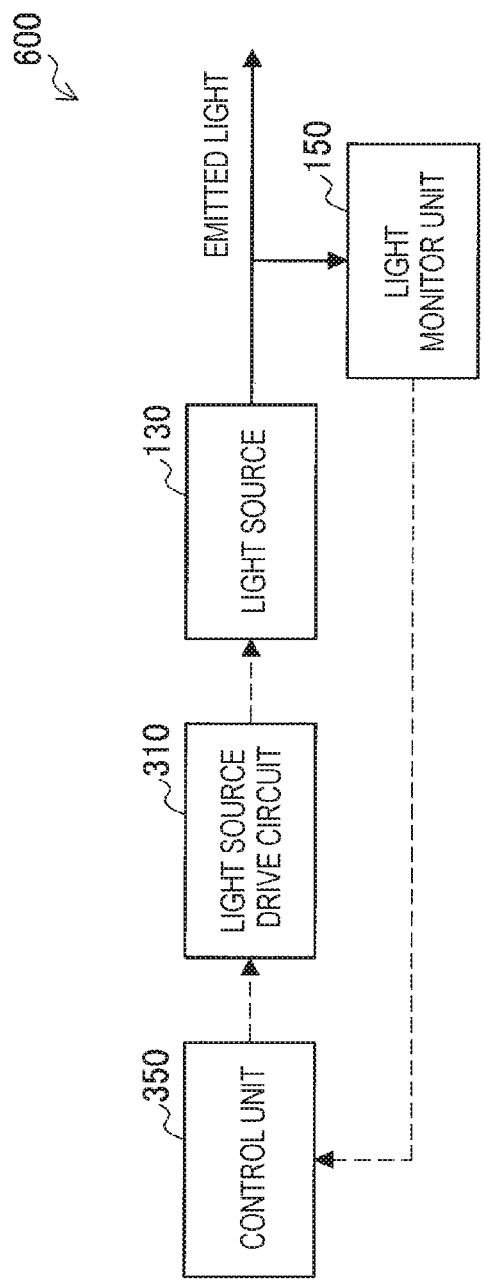
FIG. 15 is block diagram illustrating a light source device according to a second modified example.

FIG. 15 is block diagram illustrating a configuration example of a light source device 600 according to a second modified example. The light source device 600 according to the second modified example differs from the light source device 300 according to the embodiment described above in that one light source 130 is provided.

The light source device 600 includes a light source 130, a light source drive circuit 310, a light monitor unit 150, and a control unit 350. The light source device 600 according to the second modified example is provided with the one light source 130, and therefore is not provided with a multiplexing unit. The light source 130, the light source drive circuit 310, and the light monitor unit 150 can basically be configured similar to the light source 130, the light source drive circuit 310, and the light monitor unit 150 according to the embodiment described above. The color (wavelength) of light emitted from the light source 130 may be selected, as appropriate, according to the use. Also, the control unit 350 can also be configured so as to perform a learning process, drive control, and a deterioration determination process, similar to the control unit 330 according to the embodiment described above.

According to the light source device 600 according to the second modified example, effects similar to the effects obtained by the light source device 600 according to the embodiment described above can be obtained even with the light source device 600 that includes the one light source 130.

The preferred embodiments of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, in the embodiment described above, the warning unit 336 performs the secondary warning, and limits the upper limit of the output level of the light source device 300, but the technology of the present disclosure is not limited to this example. The warning unit 336 may only either perform the secondary warning or limit the upper limit of the output level of the light source device 300.

Also, in the embodiment described above, the drive currents $I_r$, $I_g$, and $I_b$ of the each of the light sources 130 are controlled such that the detection values $P_r$, $P_g$, and $P_b$ from the light monitor units 150 come to match the target values $P''_R$, $P''_G$, and $P''_B$, and the deterioration determination process is performed on the basis of the values of the drive currents $I_r$, $I_g$, and $I_r$, but the technology of the present disclosure is not limited to this example. For example, the applied voltage of each of the light sources 130 may be controlled such that the detection values $P_r$, $P_g$, and $P_b$ from the light monitor units 150 come to match the target values $P''_R$, $P''_G$, and $P''_B$, and the deterioration determination process may be performed on the basis of the applied voltage. In this case as well, if a maximum applied voltage able to be applied is set, a learning process, drive control, and a deterioration determination process similar to those of the embodiment described above can be executed and similar effects can be obtained.

Also, in the embodiment described above, the plurality of light sources 130 are controlled by one control unit 330, but the technology of the present disclosure is not limited to this example. For example, each of the plurality of light sources 130 may controlled by an independent control unit.

Also, in the embodiment described above, the red light source drive circuit 310R, the green light source drive circuit 310G, and the blue light source drive circuit 310B that drive the red light source 130R, the green light source 130G, and blue light source 130B, respectively, are provided, but the technology of the present disclosure is not limited to this example. For example, the light source device may be a continuous irradiation type light source device in which a plurality of light sources are driven by one drive circuit. In this case, a common variable constant current source is connected to each light source, and a variable resistor is connected to each light source, and a current value to be supplied to each light source can be controlled by adjusting the resistance value of each variable resistor. Therefore, a warning can be issued to the user in accordance with the actual deterioration state of the light source, while detecting the light amount of light emitted from each light source with a light monitor unit, and controlling the current supplied to each light source such that the detection value comes to match the target value.

Also, in the embodiment describe above, a description has been given using the continuous irradiation type light source device as one example, but the technology of the present disclosure is not limited to this example. For example, the light source device may be a time-shared irradiation type light source device that irradiates red light, green light, and blue light in a time-shared manner, and generates a color image on the basis of image information from light of each color received by an imaging element. In this case, the current values when the light sources of each color are made to emit light can be controlled individually. Therefore, a warning can be issued to the user in accordance with the actual deterioration state of the light source, while detecting the light amount of light emitted from each light source with a light monitor unit and controlling the drive current of each light source such that the detection value comes to match the target value.

Also, in the embodiment described above, an example in which the light source device 300 is applied to the imaging system 20 is described, but the use of the light source device 300 is not limited to an imaging system. The light source device 300 can be applied to various kinds of systems as long as the system is a system capable of using the light source device 300 provided with a light source in which the light amount of emitted light can be electrically adjusted.

Further, the effects described in this specification are merely illustrative or exemplified effects, and are not limitative. That is, with or in the place of the above effects, the technology according to the present disclosure may achieve other effects that are clear to those skilled in the art from the description of this specification.

INDUSTRIAL APPLICABILITY

Additionally, the present technology may also be configured as below.

(1)

A light source device including: at least one light source; a light monitor unit that detects emitted light emitted from the light source; a light source drive unit that controls a drive current or an applied voltage of the light source such that a detection value detected by the light monitor unit indicates a predetermined target value; and a warning unit that performs a primary warning when the drive current or the applied voltage of the light source reaches a predetermined reference value, and performs a predetermined process on a basis of a deterioration level of the light source after the primary warning is performed.

(2)

The light source device according to (1), in which the warning unit performs the primary warning when the drive current or the applied voltage of the light source reaches a preset maximum drive current or a preset maximum applied voltage.

(3)

The light source device according to (1) or (2), in which the warning unit performs the predetermined process on a basis of a decrease in the detection value of the light monitor unit.

(4)

The light source device according to any one of (1) to (3), in which the warning unit performs a secondary warning that informs a user of the deterioration level of the light source, as the predetermined process.

(4)

The light source device according to any one of (1) to (4), in which the warning unit prohibits driving of the light source beyond a predetermined output, as the predetermined process.

(6)

The light source device according to (5), in which the warning unit prohibits the driving of the light source beyond the predetermined output, by causing the target value to be reduced.

(7)

The light source device according to (6), in which the warning unit causes the target value to be gradually reduced in accordance with the deterioration level of the light source.

(8)

The light source device according to (6) or (7), in which the light source drive unit drives the light source such that the detection value detected by the light monitor unit comes to match the target value corresponding to a target output level selected from among a plurality of output levels, and the warning unit causes the target output level to decrease in stages.

(9)

The light source device according to (8), including: a learning unit that learns the detection value detected by the light monitor unit for each of the output levels, before the light source deteriorates.

(10)

The light source device according to any one of (1) to (9), in which the light source includes a plurality of light sources capable of independently adjusting light amounts of emitted light emitted from the respective light sources.

(11)

The light source device according to (10), in which the plurality of light sources includes a red light source, a green light source, and a blue light source.

(12)

The light source device according to (10) or (11), in which the light source drive unit drives the plurality of light sources such that the detection value of the light amount of emitted light emitted from each of the plurality of light sources detected by the light monitor unit comes to match each of the target values corresponding to a target output level selected from among a plurality of output levels, and the warning unit causes the target output level to decrease on a basis of deterioration of one of the plurality of light sources.

(13)

The light source device according to (12), in which the light source drive unit drives the respective light sources, while maintaining a ratio of the detection values of the respective light amounts of emitted light emitted from the plurality of light sources.

(14)

An imaging system including: at least one light source; a light monitor unit that detects emitted light emitted from the light source; a light source drive unit that controls a drive current or an applied voltage of the light source such that a detection value detected by the light monitor unit indicates a predetermined target value; a warning unit that performs a primary warning when the drive current or the applied voltage of the light source reaches a predetermined reference value, and performs a predetermined process on a basis of a deterioration level of the light source after the primary warning is performed; and an imaging unit that images an irradiation object that is illuminated.

(15)

The imaging system according to (14), in which the imaging system is a medical endoscopic device.

REFERENCE SIGNS LIST 20 imaging system
130 light source
150 light monitor unit
200 imaging device
300, 500, 600 light source device
310 light source drive circuit
330 control unit
332 learning unit
334 light source drive unit
336 warning unit
400 operating panel
550 color sensor (light monitor unit)

The invention claimed is:

1. A light source device comprising:
at least one light source;
a light sensor that detects emitted light emitted from the light source;
a light source drive circuitry configured to control a drive current or an applied voltage of the light source such that a detection value detected by the light sensor comes to match a target value corresponding to a target output level selected from among a plurality of output levels;
a learning circuitry configured to learn the detection value detected by the light sensor for each of the output levels, before the light source deteriorates; and
a warning circuitry configured to
perform a primary warning when the drive current or the applied voltage of the light source reaches a predetermined reference value, and
on a basis of a deterioration level of the light source after the primary warning is performed,
prohibit driving of the light source beyond a predetermined output, and
decrease the target output level in accordance with the deterioration level of the light source.

2. The light source device according to claim 1, wherein the warning circuitry is configured to perform the primary warning when the drive current or the applied voltage of the light source reaches a preset maximum drive current or a preset maximum applied voltage.

3. The light source device according to claim 1, wherein the warning circuitry is configured to perform the predetermined process on a basis of a decrease in the detection value of the light sensor.

4. The light source device according to claim 1, wherein the warning circuitry is configured to perform a secondary warning that informs a user of the deterioration level of the light source, as the predetermined process.

5. The light source device according to claim 1, wherein the warning circuitry is to gradually reduce the target value to be in accordance with the deterioration level of the light source.

6. The light source device according to claim 1, wherein the warning circuitry is configured to decrease the target output level in stages.

7. The light source device according to claim 1, wherein the light source includes a plurality of light sources capable of independently adjusting light amounts of emitted light emitted from the respective light sources.

8. The light source device according to claim 7, wherein the plurality of light sources includes a red light source, a green light source, and a blue light source.

9. The light source device according to claim 7, wherein the light source drive circuitry is configured to drive each of the plurality of light sources such that the detection value of the light amount of emitted light emitted from each of the plurality of light sources detected by the light sensor comes to match each of the target values corresponding to a target output level selected from among a plurality of output levels for each of the plurality of light sources, and the warning circuitry is configured to decrease the target output level on a basis of deterioration of one of the plurality of light sources.

10. The light source device according to claim 9, wherein the light source drive circuitry is configured to drive the respective light sources, while maintaining a ratio of the detection values of the respective light amounts of emitted light emitted from the plurality of light sources.

11. An imaging system comprising:

at least one light source;

a light sensor that detects emitted light emitted from the light source;

a light source drive circuitry configured to control a drive current or an applied voltage of the light source such that a detection value detected by the light sensor comes to match a target value corresponding to a target output level selected from among a plurality of output levels;

a learning circuitry configured to learn the detection value detected by the light sensor for each of the output levels, before the light source deteriorates; and a warning circuitry configured to perform a primary warning when the drive current or the applied voltage of the light source reaches a predetermined reference value, and on a basis of a deterioration level of the light source after the primary warning is performed, prohibit driving of the light source beyond a predetermined output, and decrease the target output level in accordance with the deterioration level of the light source; and an imager that images an irradiation object that is illuminated.

12. The imaging system according to claim 11, wherein the imaging system is a medical endoscopic device.

13. The imaging system according to claim 11, wherein the system is a medical imaging system.

14. The imaging system according to claim 11, wherein the warning circuitry is to gradually reduce the target value to be in accordance with the deterioration level of the light source.

15. The imaging system according to claim 11, wherein the warning circuitry is configured to decrease the target output level in stages.

16. A method of driving a light source, the method comprising:

detecting emitted light emitted from the light source using a light sensor;

controlling a drive current or an applied voltage of the light source such that a detection value detected by the light sensor comes to match a target value corresponding to a target output level selected from among a plurality of output levels;

learning the detection value detected by the light sensor for each of the output levels, before the light source deteriorates;

performing a primary warning when the drive current or the applied voltage of the light source reaches a predetermined reference value; and on a basis of a deterioration level of the light source after the primary warning is performed, prohibiting driving of the light source beyond a predetermined output, and decreasing the target output level in accordance with the deterioration level of the light source.

17. The method according to claim 16, wherein decreasing the target output level includes gradually reducing the target value to be in accordance with the deterioration level of the light source.

18. The method according to claim 16, wherein decreasing the target output level includes reducing the target output level in stages.

* * * * *